Figure 2:
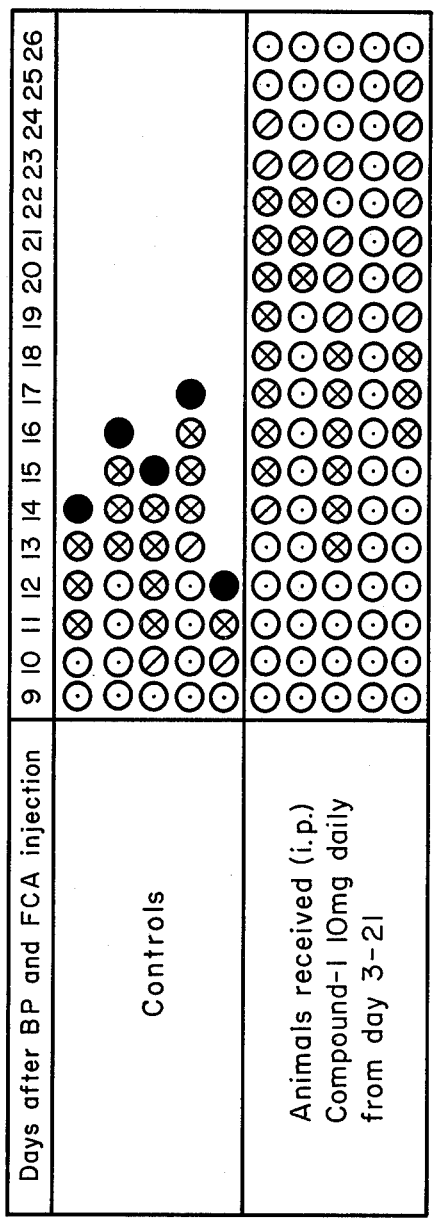

United States Patent [19]

Umezawa et al.

[11] 4,032,635
[45] June 28, 1977

[54] PHARMACEUTICAL METHOD FOR THE THERAPY OF IMMUNE DISEASES

[75] Inventors: Hamao Umezawa; Tomio Takeuchi, both of Tokyo; Akira Takamatsu, Yokohoma; Shunro Mori, Fujisawa, all of Japan

[73] Assignee: Zaidan Hojin Biseibutsu Kagaku Kenkyu Kai, Japan

[22] Filed: Feb. 24, 1976

[21] Appl. No.: 660,731

[30] Foreign Application Priority Data

June 12, 1975 Japan .............................. 50-71629

[52] U.S. Cl. ............................... 424/230; 424/324
[51] Int. Cl.$^2$ ....................................... A61K 31/60
[58] Field of Search ........................... 424/324, 230

[56] References Cited
UNITED STATES PATENTS 3,973,038   8/1976   Umezawa et al. ................ 424/324

OTHER PUBLICATIONS

Chem. Abst.–8th Coll. Index, vol. 66–75, (1967–1971), p. 27913S.

Primary Examiner—Sam Rosen
Attorney, Agent, or Firm—Herbert W. Taylor, Jr.

[57] ABSTRACT

Compounds having the formula

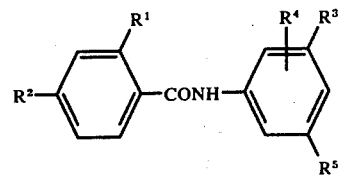

(the meanings of $R^1$, $R^2$, $R^3$, $R^4$ and $R^5$ are indicated hereinafter) exhibit suppressive activity to various immune responses and can be employed in the therapy of immunological diseases, especially autoimmune diseases.

One example is 3',5'-dichloro-2,4'-dihydroxybenzanilide having the formula

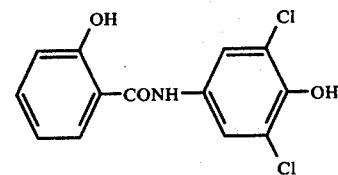

and another is 3',5'-dichloro-2,2'-dihydroxybenzanilide having the formula

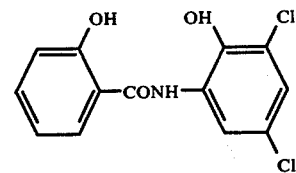

12 Claims, 3 Drawing Figures

PHARMACEUTICAL METHOD FOR THE THERAPY OF IMMUNE DISEASES

BACKGROUND OF THE INVENTION

1. Field of the Invention.

This invention relates to the use of certain chemicals of the benzanilide family in the therapy of immune diseases.

2. Description of the Prior Art.

Several attempts have been made in the prior art to find immunosuppressive agents with a specific chemotherapeutic application. Antimetabolic or antiproliferative agents that have been recognized largely from cancer screening, such as 6-mercaptopurine or cyclophosphamide, are effective in the therapy of autoimmune diseases, some infection allergies and dermatological contact allergies and act favorably to suppress transplantation immunological responses. The immunosuppressive agents that are presently employed, however, generally reveal a strong cytotoxicity and exhibit marked side effects. Thus, these drugs would not be preferable in the therapy of chronic allergic diseases or autoimmune diseases in which long-term administration may be required.

The present inventors discovered that some salicylanilide derivatives possess strong inhibitory activities toward the enzyme histidine decarboxylase which catalyzes the conversion of histidine to histamine and are useful as a therapeutic agent in allergic diseases and inflammation which may be mediated by histamine and that is disclosed in U.S. Pat. application Ser. No. 461,772 filed on Apr. 17, 1974.

It has been known that an inhibitor of histidine decarboxylase such as 2-hydrazino-3-(4-imidazolyl)-propionic acid [Chem. Abst. 76, 135672k, (1972)] or tritoqualine [Arerugi 22, 640–8 (1973) Japan] inhibits antibody formation, anaphylaxis or contact dermatitis, but these antiallergic actions may not be associated with its inhibition of histidine decarboxylase.

The present inventors further continued pharmaceological search with a series of benzanilide derivatives including the above-presented salicylanilide derivatives and others, and found that the compounds specified in this invention exhibit the suppressive effects of humoral and/or cell-mediated immunity. These compounds are not cytotoxic and have low toxicity allowing long-term administration for the therapy of such diseases as autoimmune diseases.

SUMMARY OF THE INVENTION

Accordingly, an object of the present invention has been achieved by the provision, according to the present invention, of a new pharmaceutical composition, preferably in a dosage unit form, comprising a benzanilide derivative of the following formula (I) as an active ingredient.

Another object of the present invention has been achieved by the provision, according to the present invention, of a novel method for treating various immune diseases, especially autoimmune diseases, such as multiple sclerosis, by administering a compound of the following Formula (I):

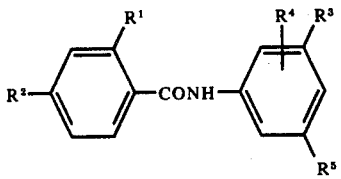

wherein $R^1$ is a hydroxy or $-O-CO-Y$ group with Y being a lower alkyl or phenyl group; $R^2$ is a hydrogen, chlorine, fluorine, trifluoromethyl or lower alkyl group; $R^3$ and $R^5$ are hydrogen, fluorine, bromine, chlorine, nitro, or lower alkyl groups; and $R^4$ is substituted at either the 2' or 4' position and is hydroxy, lower alkoxy group with 1 to 4 carbon atoms, $-O-CH_2-COOH$ or $-O-CO-Y$, Y meaning the same as above and lower alkyl as used herein being a straight or branched chain saturated hydrocarbon of 1 to 4 carbon atoms, for example, ethyl, propyl, isopropyl and the like, in combination with a pharmaceutically acceptable nontoxic carrier.

Embodiments of the present invention provide a. a pharmaceutical composition for administration of a compound of Formula (I) as an active ingredient to humans and animals in an amount sufficient to suppress the immune responses in combination with a pharmaceutically acceptable nontoxic carrier;

b. a method for chemotherapeutically treating a living animal with an immunological disorder mediated by an immediate-type or a delayed-type allergic mechanism, which comprises administering such a compound to said animals in a dosage sufficient to suppress immune responses; and c. especially a method for chemotherapeutically treating living animals with immune diseases or disorders such as contact allergic dermatitis or multiple sclerosis which comprises administering to a living animal a pharmaceutical composition to suppress the immune response comprising an effective amount of a suppressing compound of the formula

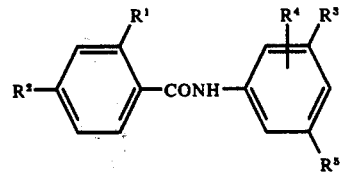

wherein $R^1$ is a hydroxy or $-O-CO-Y$ group with Y being a lower alkyl or phenyl group; $R^2$ is a hydrogen, chlorine, fluorine, trifluoromethyl or lower alkyl group; $R^3$ and $R^5$ are hydrogen, fluorine, bromine, chlorine, nitro, or a lower alkyl group and $R^4$ is substituted at either the 2' or 4' position and is hydroxy, lower alkoxy group with 1 to 4 carbon atoms, $-O-CH_2-COOH$ or $-O-CO-Y$, Y meaning the same as noted above and lower alkyl as used herein being a straight or branched chain saturated hydrocarbon with 1 to 4 carbon atoms, in combination with a pharmaceutically acceptable nontoxic carrier, and, in a preferred embodiment, the method for chemotherapeutically treating immune diseases and disorders with a compound of the formula

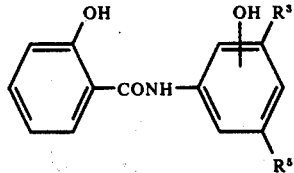

wherein $R^3$ and $R^5$ are fluorine, bromine, chlorine, nitro or lower alkyl groups, and also the method for chemotherapeutically treating immune diseases and disorders with a compound of the formula

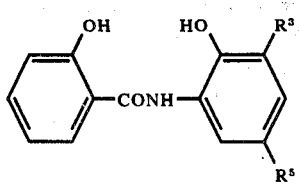

wherein $R^3$ and $R^5$ are hydrogen, chlorine, bromine, fluorine, nitro, or lower alkyl groups with 1 to 4 carbon atoms and particularly said compositions and methods wherein the immune diseases and disorders are contact allergic dermatitis, autoimmune diseases and especially multiple sclerosis, systemic lupus erythematosus, autoimmune hemolytic anemia, periarteritis nodosa and myasthenia gravis and the preferred agents are 3′, 5′-dichloro-2, 2′-dihydroxybenzanilide and 3′, 5′-dichloro-2, 4′-dihydroxybenzanilide.

The compounds of Formula (1) can be prepared by various methods. For example, a bezoic acid derivative having $R_1$ and $R_2$ groups or atoms, or a reactive derivative thereof, such as halide, which contains in the 2 position a free hydroxy group or a substituent that is convertible to a free hydroxyl group, e.g., an acyloxy group, and is otherwise unsubstituted, is reacted with a desired aniline derivative having $R_3$, $R_4$ and $R_5$ groups or atoms.

In benzanilide derivatives so obtained which contain a substituent which is convertible to a free hydroxyl-group, if desired, this substituent is then converted into the hydroxyl group.

The aforementioned reactions are carried out in known manner in the absence or presence of a diluent and/or a condensing agent. Thus, for example, in reacting a benzoic acid derivative with an aniline derivative, the reaction is advantageously carried out in the presence of a dehydrating agent, especially phosphorous trichloride or thionyl chloride in an anhydrous solvent.

Also, the compounds of Formula (1) may be readily obtained by reacting a derivative of benzoyl halide, preferably the chloride or bromide, with an appropriate aniline derivative in the presence of a suitable base, e.g., pyridine, N,N-dimethylaniline or triethylamine, in an anhydrous inert solvent.

In these condensation reactions the hydroxyl groups of the benzoic acid derivative or its halide may be protected by such groups as acetyl or other conventional protective groups which are, if desired, easily removed from the condensation product. The thus obtained compounds with a protected or unprotected hydroxyl group can be esterified by conventional techniques.

The pharmacological properties of the compounds of Formula (1) were revealed as in the following.

1. Suppression of Delayed-Type Hypersensitivity (DTH)

The compounds of Formula (I) show suppression of various delayed-type hypersensitivity. In reference to the method by Lagrange [J. Exp. Med. 139, 528 (1974)], $10^8$ sheep red blood cells (SRBC) without adjuvant were subcutaneously injected into the mouse hind footpad to immunize the animal. Four days later the animals were challenged by subcutaneous injection of $10^8$ SRBC into another footpad. DTH response was measured as the increase in the thickness of footpad 24 hours after the injection of SRBC.

Figure 1:
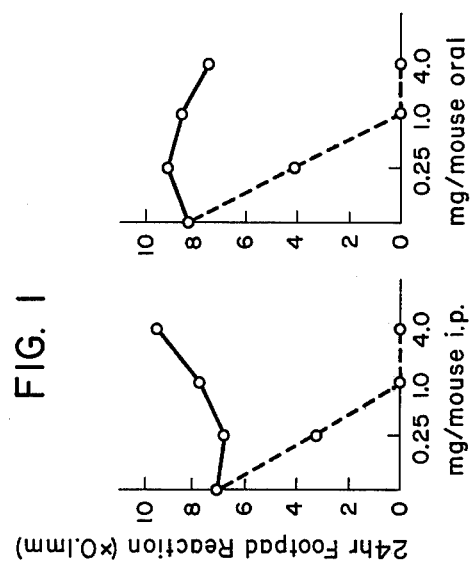

Varying doses of Compound-1 were administered orally or intraperitoneally either at the time of immunization (day 0) or challenge (day 4). As shown in FIG. 1, when Compound-1 was administered on day 4, DTH was suppressed in mice sensitized by footpad inoculation with SRBC. However it was not active when given at the time of sensitization (day 0).

In FIG. 1 the ordinate indicates the swelling ($\times 0.1$ mm.) of mice footpads on day 5 and the abscissa indicates the dose of Compound-1 per mouse administered by the oral (right) and intraperitoneal (left) routes. Solid line curve indicates the relationship when Compound-1 was administered on day 0 and the dotted line curve indicates the relationship when given on day 4.

This suppressive activity on DTH developed in mice footpad should be distinguished from a non-specific anti-inflammatory activity. Anti-inflammatory drugs such as aspirin, mefenamic acid and indomethacin as well as such protease-inhibitors as leupeptin, pepstatin and chymostatin are known to strongly suppress carrageenin-induced edema in a does of 1 mg./mouse, but they exhibit little suppression of this DTH reaction.

The rates of suppression of footpad swelling were examined for the compounds of Formula (I) and are shown in Table 1. The compounds were administered intraperitoneally in a dose 1 mg./mouse at the time of immunization (day 0) or challenge (day 4). Table 1 includes the results of humoral antibody response described later.

TABLE 1

Suppression of Various Types of Immune Response With the Compounds of Formula (I)

| Compound No. | $R^1$ | $R^2$ | $R^3$ | $R^4$ | $R^5$ | Suppression Delayed-Type Hypersensitivity Administered at Immunization | Administered at Induction | Plaque Forming Cells |
|---|---|---|---|---|---|---|---|---|
| 1 | OH | H | Cl | 4′-OH | Cl | − | +++ | +++ |
| 2 | OH | H | Cl | 2′-OH | Cl | − | +++ | +++ |
| 3 | OH | H | Cl | 4′-OCH$_3$ | Cl | − | +++ | ++ |
| 4 | OCOCH$_3$ | H | Cl | 4′-OCOCH$_3$ | Cl | − | +++ | ++ |
| 5 | OCOCH$_2$CH$_3$ | H | Cl | 4′-OCOCH$_2$CH$_3$ | Cl | − | +++ | ++ |
| 6 | OCO—⟨phenyl⟩ | H | Cl | 4′-OCO—⟨phenyl⟩ | Cl | − | +++ | +++ |
| 7 | OCOCH$_3$ | H | Cl | 2′-OCOCH$_3$ | Cl | − | +++ | ++ |
| 8 | OCOCH$_3$ | H | Cl | 4′-OH | Cl | − | − | + |
| 9 | OH | H | Cl | 4′-OCH$_2$COOH | Cl | − | +++ | − |
| 10 | OH | F | Cl | 4′-OH | Cl | − | +++ | + |
| 11 | OH | CH$_3$ | Cl | 4′-OH | Cl | +++ | − | + |
| 12 | OH | H | Br | 4′-OH | Br | +++ | ++ | − |
| 13 | OH | H | Br | 2′-OH | Br | ++ | ++ | − |

TABLE 1-continued
Suppression of Various Types of Immune Response With the Compounds of Formula (I)

| Compound No. | $R^1$ | $R^2$ | $R^3$ | $R^4$ | $R^5$ | Suppression Delayed-Type Hypersensitivity Administered at Immunization | Administered at Induction | Plaque Forming Cells |
|---|---|---|---|---|---|---|---|---|
| 14 | OH | H | Br | 4'-OCH$_2$CH$_3$ | Br | ++ | +++ | − |
| 15 | OCOCH$_2$CH$_3$ | H | Br | 2'-OCOCH$_2$CH$_3$ | Br | ++ | ++ | − |
| 16 | OH | CH$_3$ | Br | 4'-OH | Br | ++ | +++ | − |
| 17 | OH | H | F | 4'-OH | Cl | − | +++ | +++ |
| 18 | OH | Cl | Cl | 4'-OCH$_3$ | F | − | +++ | + |
| 19 | OH | H | CH$_3$ | 2'-OH | Cl | − | + | + |
| 20 | OH | H | Cl | 2'-OH | CH$_3$ | − | +++ | ++ |
| 21 | OH | H | NO$_2$ | 2'-OH | NO$_2$ | ++ | +++ | − |
| 22 | OH | H | Cl | 4'-OH | H | − | − | +++ |
| 23 | OH | H | Cl | 2'-OH | H | − | − | ++ |
| 24 | OH | F | Cl | 4'-OCH$_2$CH$_3$ | H | − | ++ | + |
| 25 | OCOCH$_3$ | H | Cl | 2'-OCOCH$_3$ | H | − | + | ++ |
| 26 | OH | H | H | 4'-OH | H | − | ++ | ++ |
| 27 | OH | H | H | 4'OCH$_3$ | H | − | +++ | +++ |
| 28 | OH | F | H | 4'-OCH$_3$ | H | − | +++ | +++ |
| 29 | OH | CH$_3$ | H | 4'-OCH$_3$ | H | − | +++ | + |
| 30 | OH | CD$_3$ | H | 4'-OCH$_3$ | H | + | +++ | + |
| 31 | OH | F | H | 4'-OCH$_2$CH$_3$ | H | − | +++ | ++ |
| 32 | OCOCH$_3$ | CH$_3$ | H | 4'-OCH$_3$ | − | + | − | |

NOTE: Suppression rate:
0 – 25%    +
25 – 50%   +
50 – 75%   ++
75% over   +++

2. Suppression of Experimental Allergic Encephalomyelitis

Another aspect of pharmacological effects of the compounds of this invention was demonstrated by their effectiveness in suppressing experimental allergic encephalomyelitis (EAE) in guinea pigs.

By injecting basic protein (B.P.) the extract from central nervous tissue, together with Freund's complete adjuvant, a typical EAE symptom develops. Guinea pigs show drastic reduction of body weight and development of paralysis about ten days after injection with BP and they finally die within 17 days after the injection of BP.

On the other hand among five animals receiving 10 mg. of Compound-1 intraperitoneally once daily from 3 to 21 days after antigen (BP) injection, one gave no sign of the development of paralysis and four others showed paralysis to a certain degree at 13–16 days but the symptoms of EAE soon disappeared. Even after discontinuation of Compound-1, no more paralytic symptoms recurred in these animals.

FIG. 2 shows the suppressive effect of Compound-1 on EAE (experimental allergic encephalomyelitis) in guinea pigs in which ⊘ shows slight paralysis in hind paw
⊗ shows paralysis in both hind paws
✹ shows paralysis extending to forelimbs
✹ shows a moribund condition
● shows death and FCA means Freund's Complete Adjuvant (tubercular bacilli = TB 100 mcg.) and figures show days elapsed.

3. Suppression of Contact Allergy in Guinea Pigs

The compound of Formula (I) significantly suppressed contact allergy in guinea pigs which was induced by dinitrochlorobenzene (DNCB). For example, approximately 0.1 ml. of a 10% solution of DNCB in acetone was administered percutaneously on the ear. Fourteen days later animals were skin tested on a shaved flank by topical spotting (about 0.05 ml.) of a 0.1% solution of DNCB in acetone. Skin lesions were evaluated and scored 24 hours later as follows:

+ = slight erythema
++ = marked erythema and slight swelling
+++ = marked induration and swelling Guinea pigs readily develop contact hypersensitivities of the delayed-type by simple topical application of DNCB. As shown in Table 2, intraperitoneal treatment with Compound-1 or Compound-2 in a dose of 100 mg./kg. at 0.5, 24 and 48 hours before challenge resulted in significant inhibition of the response to DNCB in sensitized guinea pigs.

TABLE 2

| Compound No. | Inhibition of the Expression of Contact Hypersensitivity in Guinea Pigs Skin Lesion Score Animal No. | | |
|---|---|---|---|
| | 1 | 2 | 3 |
| None | +++ | +++ | +++ |
| −1 | + | + | ++ |
| −2 | + | ++ | ++ |

4. Suppression of Anaphylactic Shock in Mice

The compounds of Formula (I) also exhibit suppression of systemic anaphylactic shock in mice. Suppression was obtained on both occasions when the compound was administered at the time of immunization or challenge.

The mice were immunized by a subcutaneous injection of a mixture of 0.1 ml. (100 mcg.) egg albumin and 0.1 ml. Freund's complete adjuvant, and used for experiment four months thereafter. In control mice sensitized in the above manner, the shock symptom emerged after induction by intravenous injection of 100 mcg. egg albumin and most of the animals died from shock within about 40 minutes.

Table 3A show the suppression effect with Compound -1 when given as a single does (0.25 or 1.0 mg./mouse, i.p.) at the time of sensitization. Table 3B shows the effect of representative compounds of Formula (I) when given in a dose of 1 mg./mouse, i.p. 0.5 and 5 hours before challenge. In the animals receiving the test drug, the time until death after induction was somewhat delayed and most of the animals survived the shock.

TABLE 3A

Suppression of Anaphylactic Shock in Mice

| Compound-1* | Animal No. | | | | | |
|---|---|---|---|---|---|---|
| | 1 | 2 | 3 | 4 | 5 | 6 |
| 0.25 mg./mouse | 18 | 21 | 22 | SV | SV | SV |
| 1.0 mg./mouse | 22 | 23 | 30 | SV | SV | SV |
| Control | 16 | 25 | 27 | 30 | 33 | 37 |

*Administered i.p. at the time of sensitization

TABLE 3B

Suppression of Anaphylactic Shock

| Compound No. | Mouse No. | | | | |
|---|---|---|---|---|---|
| | 1 | 2 | 3 | 4 | 5 |
| −1* | 35 | SV | SV | SV | SV |
| −2* | 10 | 35 | SV | SV | SV |
| −21* | SV | SV | SV | SV | SV |
| −27* | SV | SV | SV | SV | SV |
| Control | 15 | 18 | 20 | 30 | SV |

*Administered i.p. at 0.5 and 5 hours before challenge.
SV indicates the mouse survived the shock.
Numerical values indicate the time of death (in minutes) after induction.

5. Suppression of Passive Cutaneous Anaphylaxis (PCA)

The compounds of Formula (I) are active in suppressing passive cutaneous anaphylaxis (PCA) in guinea pigs. Guinea pigs received intradarmally serial dilutions of antiserum (0.1 ml.), which was obtained from guinea pigs immunized with a mixture of egg albumin and Freund's complete adjuvant. At the time of sensitization with antiserum, the compound of Formula (I) was administered either orally (100 mg./kg.) or intraperitoneally (50 mg./kg.).

Four hours later the animals were challenged by intravenous injection of a mixture of 5 mg. egg albumin and Evans blue dye. The reaction was measured 30 minutes later by the blue zone which emerged at the point of antiserum injection.

Table 4 shows the results of the maximum dilution of antiserum giving a 10 mm. diameter blue zone indicating suppression of PCA in guinea pigs with these compounds.

TABLE 4

Suppression of PCA in Guinea Pigs

| Compound No. | Max. Dilution of Antiserum | | |
|---|---|---|---|
| | Oral (100 mg./kg.) | i.p. | (50 mg./kg.) |
| Control | 1060 | 1024 | 1350 |
| −1 | 548 | 64 | 315 |
| −2 | 736 | | |
| −12 | 548 | | |
| −27 | 284 | | |

6. Suppression of Antibody Formation

The compounds of Formula (I) suppress the primary antibody formation. $10^8$ sheep red blood cells (SRBC) were injected intravenously into ddY-strain mice to immunize the animals, when the compounds of Formula (I) were administered intraperitoneally.

Four days later, the spleen cells of mice with the antibody forming activity were isolated and examined by Jerne's method. For example $10^8$ SRBC were intravenously injected for immunization and 1000 mcg., 250 mcg., 62.5 mcg. and 15.6 mcg./mouse of Compound-1 (cf. Table 1) was given intraperitoneally.

Figure 3:
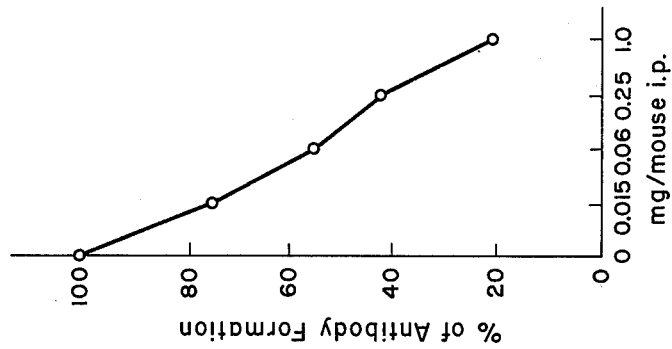

FIG. 3 shows the effect of Compound-1 on the primary antibody formation of mice in which the ordinate is the rate of antibody formation in percent, and the abscissa the dose (i.p.) of Compound-1 per mouse.

As shown in FIG. 3, the primary antibody formation in spleen cells of treated mice was apparently suppressed in proportion to increased amounts of Compound-1.

Additional experiment to evaluate the effect of Compound-1 on primary antibody formation was made by spleen cell culture in vitro. According to the method described by Mishell and Dutton [J. Exp. Med., 126, 423 (1967)], dissociated spleen cells prepared from normal mice spleens were cultured with SRBC as antigen and at initiation of cultures Compound-1 was added, and then four days later, antibody formation in cultures was determined by Jerne's hemolytic plaque assay. When Compound-1 was added to the spleen cell culture, the number of plaque forming cells was significantly decreased, but there were no changes in the number of nucleated cells nor in the viable cell count in the cultures.

Consequently Compound-1 is not cytotoxic nor antiproliferative in vitro and the suppressive effect on antibody formation is not attributable to cytotoxicity.

The suppression rate of primary antibody formation with the benzanilide derivatives of Formula (I) is presented in Table 1. Each compound was administered intraperitoneally in the dosage of 1 mg./mouse.

7. Acute Toxicity in Mice

Acute toxicological studies were carried out on mice by intraperitoneal administration of the compounds of Formula (I). The approximate $LD_{50}$ values for representative compounds are given as follows:

| Compound No. | $LD_{50}$ (mg./kg.) |
|---|---|
| 1 | 2,400 |
| 2 | 2,500 |
| 6 | 2,800 |
| 7 | >3,000 |
| 12 | 1,100 |
| 13 | 1,280 |
| 15 | 2,200 |
| 19 | 1,800 |
| 23 | 1,550 |
| 25 | 2,500 |
| 27 | >3,000 |
| 28 | 2,800 |
| 29 | 2,500 |
| 30 | 2,400 |

Compound-1 and Compound-2 were given orally or intraperitoneally to rats in daily doses of 12.5, 50 or 200 mg./kg., respectively, for one month. The weight gain was normal and no particular symptoms or abnormality attributable to the drug dosage was noted.

Compounds of Formula (I) in general have a low acute to subacute toxicity profile.

Such immunosuppressive agents as cyclophosphamide, 6-mercaptopurine or azathioprine are antiproliferative and antimetabolic agents which disrupt nucleic acid and/or protein synthesis and, as the consequence, inhibit both humoral and cell-mediated immunities, but these drugs are effective in general only at near-lethal doses owing to their cytotoxicity.

On the contrary the compounds of Formula (I) differed from the presently defined immunosuppressive agents and are neither cytotoxic nor antiproliferative. Therefore, the effects of these compounds on immune respones are not so drastic as cytotoxic immunosuppressive agents, but significantly suppress humoral immunological response and/or cell-mediated immune responses without any evidence of toxicity.

It was assumed that compounds of this invention exert effects on immune responses by interfering with the antigen-processing by macrophage, interaction between T and B-cells or by impeding the binding of antibody with mast cells or binding of antigen with sensitized lymphocytes.

The compounds also exert a significant stabilizing influence on cell membranes; for instance Compound-1 suppressed the heat-induced hemolysis of red blood cells to about the same extent as did mefenamic acid or indomethacin, which may explain one mode of action, EAE is considered to be one of autoimmune diseases of the central nervous system and a comparable model in animal to multiple sclerosis (MS) in humans. It has been known that such immunosuppressive agents as 6-mercaptopurine or cyclophosphamide can suppress the development of EAE when they are given at such high doses as would cause toxicity due to their cytotoxic properties, but after discontinuation of the drug and following a latent period the animals often develop paralytic EAE.

Contrastingly, the subject compounds of Formula (I) of this invention, particularly compound-1 exhibit a potent suppressive effect on EAE developed in guinea pigs without recrudescence of paralysis after discontinuation of the drug, and are supposed to be a useful drug for treating multiple sclerosis (MS) and other related autoimmune diseases.

Steroids, ACTH or some immunosuppressive agent are presently applied to patients with MS and related autoimmune diseases, but their effects are limited due to serious side-effects caused by long-term administration of the drug. These drugs are unable to prevent recrudescence and practically no effective therapy of MS has yet been established.

According to the results described above, it was indicated that the subject compounds of Formula (I) are therapeutically effective in such diseases mediated by delayed-type immune mechanism as autoimmune diseases: multiple sclerosis, rheumatic fever, rheumatoid arthritis, systemic lupus erythematosus, progressive systemic sclerosis, allergic nephritis, autoimmune hemolytic anemia, leucopenia, idiopathic thrombocytopenic purpura, multiple periarteritis nodosa, myasthenia gravis, dermatomyositis and the like.

Effectiveness would also be indicated for these compounds in the field of allergic contact dermatitis and in transplant rejection.

Moreover it can be expected based on the effect on humoral antibody responses that the compounds of Formula (I) are useful for treating such immediate type immune diseases as bronchial asthma, nettle rash, hay fever, allergic rhinitis, allergic gastritis and the like in which humoral antibodies play possible roles.

(PHARMACEUTICAL COMPOSITIONS)

The novel pharmaceutical compositions of this invention can be employed in the therapy of various immune diseases, especially autoimmune diseases mediated by delayed-type allergic reactions.

To prepare the pharmaceutical compositions of this invention, the compound of Formula (I) is combined as the active ingredient in an intimate admixture with a pharmaceutical carrier according to conventional pharmaceutical compounding techniques.

In practice, the medical drug contains one or more benzanilide compounds of formula (I) as the active ingredient, and is applied parenterally or non-parenterally in either solid or liquid form. The solid forms for oral use are compressed tablets, capsules, granules, powders and troches. They contain one or more compounds of Formula (I) as the active ingredient and proper powder vehicles such as lactose, sucrose, sorbitol, mannitol, starch, calcium carbonate, amylopectin and cellulose derivatives and additives such as lubricants and binders, if necessary. By adding a suitable basic buffer such as sodium monophosphate and by entero-coating, tablets which are well-utilized in the enteric tract can be formulated.

The liquid compositions for oral use take the form of suspension, solution, homogenate and syrup which contain, in addition to the active ingredient, conventional inactive diluents such as water, ethanol, glycerin, propyleneglycol and so on. Some proper dissolution agents, suspending agents, sweeteners, and the like can be used if needed.

The compounds of this invention are generally slightly soluble in water. Therefore to prepare the liquid form for injection use, such solvents as ethanol, propylene glycol, physiologically inactive amino alcohols like monoethanol amine, diethanol-amine and triethanol-amine, sugar amines such as glucamine, N-methyl glucamine and methyl glucosamine are added to increase the solubility of the active ingredient in sterile distilled water. The suspensions for injection contain conventionally used sterile carriers for suspension and additives such as dispersant, suspending agent, stabilizer and an agent to reduce pain. The solution and the suspension for injection should be prepared under sterile conditions and enclosed in ampoules or vials.

Non-parenteral formulation other than injectable preparations include suppositories and ointments. To prepare suppositories, various base carriers such as cacao butter can be employed, together with proper additives such as emulsifying agents and preservatives. They are admixed with the compound of this invention which is prepared as a fine powder. The ointment is also prepared with various base carriers such as wax, fat, lanolin, petrolatum (vaseline), paraffin, glycols and higher alcohols, together with proper additives. Emulsion-type base, such as absorption ointments or hydrophylic petrolatum are preferably used. They are admixed with the finely powdered active ingredient.

The content of the active ingredient of this invention in the above-mentioned pharmaceutical preparations varies according to the purposes and conditions of therapeutic application. Furthermore, the regimen and the dose schedule should be decided after taking into account the kind of disease or disorder, the symptoms, the route of administration, the age and weight of a pateint and other factors.

The pharmaceutical compositions herein will contain per dosage unit, e.g., tablet, capsule, injection, or the like, from about 10 to 500 mg. of a compound of Formula (I) as an active ingredient, and preferably from about 20 to 300 mg. of said compound.

With the oral preparations or the suppository, the amount of administered active ingredient of this invention is 10–500 mg. daily for adult patients, preferably 20–300 mg. The preferred administration schedule is daily or in 2–3 day intervals. With the injectable preparations the intramuscular route is most preferred but intravenous and intra-articular applications can also be employed. The daily dose is 20–500 mg. in one injection or 2 to 3 portions. The ointments which are preferably applied to allergic dermatitis such as allergic contact dermatitis and nettle rash are prepared in a 1–20% concentration, preferably a 2–10% concentration of the active ingredient and are applied directly onto the affected surface.

EXAMPLE 1

3',5'-Dichloro-2,4'-dihydroxybenzanilide (Compound-1)

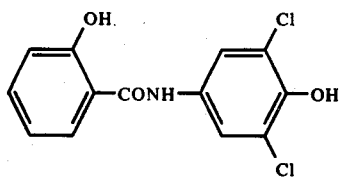

2,6-Dichloro-4-aminophenol (0.37 g.) was dissolved in acetone (30 ml.) to which pyridine (0.32 ml.) was added. While mixing, an acetone solution (10 ml.) of the acid chloride prepared from acetylsalicylic acid (0.38 g.) was added by drops. After the reaction was completed, the solution was evaporated under reduced pressure and the residue was dissolved in ethyl acetate and then was washed with water then with 1N-hydrochloric acid. After evaporating off the ethyl acetate under reduced pressure the resulting residue was dissolved in a mixture of methanol and 2N-sodium hydroxide (10 ml. each). The solution was agitated for several hours then acidified with 2N-hydrochloric acid to precipitate the product. By recrystallization in acetone-water, white needle-like crystals of 3',5'-dichloro-2,4'-dihydroxybenzanilide (0.62 g.) were obtained. The yield was 78% and the melting point was 217–219° C.

EXAMPLE 2

3',5'-Dichloro-2,2'-dihydroxybenzanilide (Compound-2)

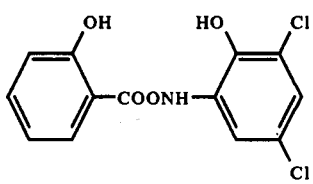

Acetylsalicyclic acid (1.73 g.) was admixed with thionyl chloride (10 ml.) and stirred overnight at 35° C. After the reaction was completed, the excess thionyl chloride was removed by evaporation under reduced pressure. The residue, crude acetylsalicyloyl chloride, was admixed with acetone (20 ml.) to make a uniform solution.

Then 6-amino-2,4-dichlorophenol (1.7 g.) and N,N-dimethylaniline (2.5 ml.) were dissolved in acetone (30 ml.) which was cooled at 0° to 5° C. Into this solution the acetone solution of acetylsalicyloyl chloride was added by drops. The solution was warmed up to room temperature and condensed by evaporation under reduced pressure. The residual oily condensate thus obtained was admixed with 2N sodium hydroxide solution (30 ml.) and stirred at room temperature. After the deacetylation reaction was completed, acidification of the solution with hydrochloric acid gave a precipitate which was subjected to decolorization with active charcoal and then recrystallized from aqueous acetone to give colorless, needle-like crystals (1.4 g ) of 3',5'-dichloro-2,2'-dihydroxybenzanilide. Yield: 49%. The melting point of the product is 222°–223° C.

EXAMPLE 3

3',5'-Dibromo-2,4'-dihydroxybenzanilide (Compound-12)

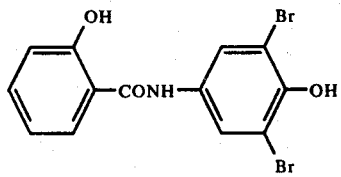

2,6-Dibromo-4-aminophenol (0.6 g.) was dissolved in acetone (30 ml.) to which pyridine (0.32 ml.) was added. Then the solution was added by drops and with stirring to an acetone solution (10 ml.) containing acetylsalicyloyl chloride which was prepared from acetylsalicylic acid (0.38 g.). The resulting solution was evaporated to dryness under reduced pressure to give a residue which was dissolved in ethyl acetate. After washing first with water and then with 1N hydrochloric acid the solution was evaporated under reduced pressure to remove the ethyl acetate. the residue was redissolved in a mixture of methanol and 2 N sodium hydroxide (10 ml. each). Stirring this solution for several hours and acidifying with 2 N hydrochloric acid precipitated the product which was recrystallized from aqueous methanol to give light brown crystals of 3',5'-dibromo-2,4'-dihydroxybenzanilide (0.88 g.). Yield: 78%. The melting point of the compound is 182°–187° C.

EXAMPLE 4

2,4'-Diacetoxy-3',5'-dichlorobenzanilide (Compound-4)

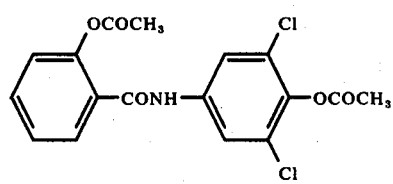

Acetylsalicylic acid chloride prepared from acetylsalicylic acid and thionyl chloride was condensed with 4-amino-2,6-dichlorophenol followed by deacetylation to yield 3',5'-dichloro-2,4'-dihydroxybenzanilide (4 g.).

Then the compound was dissolved in acetic anhydride acid (50 ml.) and 3 drops of concentrated sulfuric acid were added with mixing followed by standing at 5°–6° C. for 1 to 2 hours. Then the addition of ice-cold water (500 ml.) gave a white precipitate which was separated, rinsed with water and dried. Finally the precipitate was recrystallized from methanol and white needle crystals of 2,4'-diacetoxy-3',5'-dichlorobenzanilide (3.65 g.) were obtained. The yield was 71.1% and the melting point of the product was 154°–156° C.

EXAMPLE 5

2-Hydroxy-4'-methoxybenzanilide (Compound-27)

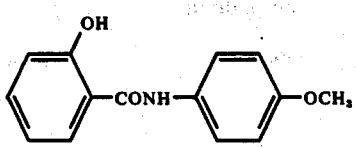

Acetylsalicylic acid (5 g.) was dissolved in thionyl chloride (200 ml.) and agitation was carried out overnight at room temperature. After the removal of thionyl chloride by evaporation under reduced pressure the residue was redissolved in acetone (50 ml.) which was added by drops at room temperature to an acetone solution (200 ml.) contaning p-anisidine (3.4 g.) and pyridine (4.5 g.). After further agitation for 1 to 2 hours the condensation reaction was completed. After evaporation under reduced pressure the residue was dissolved in ethyl acetate, and the solution was extracted with water and then with 1N hydrochloric acid to remove impurities. After drying under reduced pressure, the residue was dissolved in a small amount of methanol, to which a 2N sodium hydroxide solution (250 ml.) was added with agitation and was kept for 2 hours at room temperature. By acidifying with 2N hydrochloric acid, crystals (4.2 g.) of the demasked compound 2hydroxy-4'-methoxybenzanilide were obtained by recrystallization from an acetone-water mixture. Yield: 62%, melting point: 162°–163° C.

EXAMPLE 6

2-Hydroxy-4-methyl-4'-methoxybenzanilide (Compound-29)

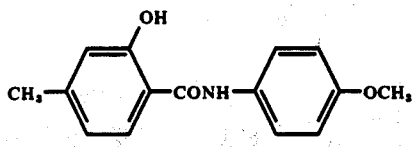

4-Methyl-acetylsalicylic acid (5 g.) was converted to its acid chloride by a conventional method and dissolved in acetone (200 ml.). Then p-anisidine (3.2 g.) and dimethylaniline (3.1 g.) were dissolved in acetone (100 ml.) and the above acid chloride solution was added by drops while cooling and mixing; agitation was maintained for 1 to 2 hours. Then the reaction mixture was concentrated under reduced pressure, and the residue was dissolved in ethyl acetate and treated as in the similar method of Example 5 to give 2-hydroxy-4-methyl-4'-methoxybenzanilide (5.3 g.). Yield: 80%, melting point: 185°–186° C.

EXAMPLE 7

(Pharmaceutical Compositions)

1. Capsules

Ten thousand hard gelatin capsules each containing 50 mg. of 3',5'-dichloro-2,4'-dihydroxybenzanilide (Compound-1) as the active ingredient (A.I.) are prepared from the following formulation:

|  | Grams |
| --- | --- |
| A.I. | 500 |
| Lactose | 1,500 |
| Starch | 400 |
| Talc | 400 |
| Magnesium stearate | 10 |

A uniform mixture of the active and supplementary ingredients is prepared and placed into capsules.

2. Tablets

Ten thousand compressed tablets each containing 100 mg. of 3',5'-dichloro-2,4'-dihydroxybenzanilide (Compound-1) as the active ingredient are prepared from the following formulation:

|  | Grams |
| --- | --- |
| A.I. | 1,000 |
| Na$_2$HPO$_4$ | 1,000 |
| Avicel | 750 |
| Starch | 500 |
| Talc | 70 |
| Magnesium stearate | 30 |
| Carboxyl methylcellulose | 150 |

Finely powdered ingredients are mixed, granulated and compressed into tablets by the use of conventional methods. Entero-coating processes are applied as needed.

3. Injectable Solution

The following formulation provides one liter of a parenteral solution comprising 20 mg. of 3',5'-dichloro-2,4'-dihydorxybenzanilide (Compound-1) as the active ingredient per milliliter.

|  | Grams |
| --- | --- |
| A.I. | 20 |
| N-methylglucamine | 30 |
| Sodium sulfite | 1 |
| Water for injection to make a total of 1 liter |  |
| pH | 8.5 – 9.0 |

The active ingredients slightly soluble in water were dissolved by the addition of organic amines or propylene glycol. The solution is autoclaved to insure sterility and placed into sterile vials under a nitrogen gas envelopment.

4. Ointment

The following formulation provides 100 g. of ointment suitable for topical application comprising 5% of 3',5'-dichloro-2,4'-dihydroxybenzanilide (Compound-1) as an active ingredient:

|  | Grams |
| --- | --- |
| A.I. | 5 |
| Absorption ointment base | 95 |

Finely powdered Compound-1 and a suitable ointment base are mixed well to make a uniform paste by a usual incorporation method.

5. Suppository

The following formulation provides 100 g. of suppositories comprising 50 mg. of 3',5'-dichloro-2,4'-dihydroxybenzanilide (Compound-1) as an active ingredient per gram.

|  | Grams |
|---|---|
| A.I. | 5 |
| Cacao butter | 65 |
| White beeswax | 10 |
| Emulsifying Agent [EMULGEN-408 (Trade name KAO ATLAS CO., INC.)] | 5 |
| Water | 15 |

The active ingredient (A.I.) in fine powder form was thoroughly and uniformly mixed with such conventially-used suppository bases as cacao butter or lanolin and formulated by the conventionally-used methods for suppository formulation.

We claim:

1. The method for chemotherapeutically treating immune diseases and disorders which comprises administering to a living animal a pharmaceutical composition to suppress the immune response comprising an effective amount of a suppressing compound of the formula

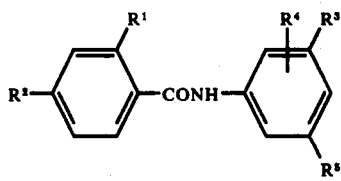

wherein $R^1$ is hydroxy; $R^2$ is hydrogen, chlorine, fluorine, trifluoromethyl or lower alkyl; $R^3$ and $R^5$ are hydrogen, fluorine, bromine, chlorine, nitro, or lower alkyl and $R^4$ is substituted at either the 2' or 4' position and is hydroxyl or lower alkoxy with 1 to 4 carbon atoms and lower alkyl as used herein being a straight or branched chain saturated hydrocarbon with 1 to 4 carbon atoms in combination with a pharmaceutically acceptable nontoxic carrier.

2. The method for chemotherapeutically treating immune diseases and disorders according to claim 1 wherein said compound is a compound of the formula

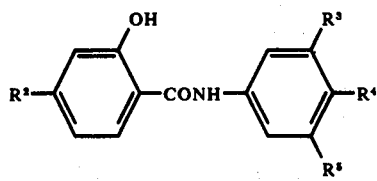

wherein $R^2$ is hydrogen, chloring, fluorine, trifluoromethyl or lower alkyl; $R^3$ and $R^5$ are hydrogen, fluorine, bromine, chlorine, nitro or lower alkyl and $R^4$ is hydroxyl or lower alkoxy with 1 to 4 carbon atoms with lower alkyl as used herein being a straight or branched chain saturated hydrocarbon with 1 to 4 carbon atoms.

3. The method for chemotherapeutically treating immune diseases and disorders according ato claim 2 werein said compound is 3',5'-dichloro-2,4'-dihydroxybenzanilide.

4. The method for chemotherapeutically treating immune diseases and disorders according to claim 1 wherein said compound is a compound of the formula

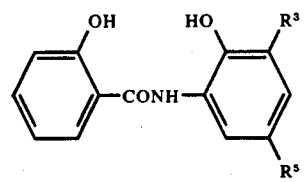

wherein $R^3$ and $R^5$ are hydrogen, chlorine, bromine, fluorine, nitro, or lower alkyl groups with 1 to 4 carbon atoms.

5. The method for chemotherapeutically treating immune diseases and disorders according to claim 4 wherein said compound is 3',5'-dichloro-2,2'-dihydroxybenzanilide.

6. The method for chemotherapeutically treating immune diseases and disorders according to claim 1 in which the immune diseases and disorders are autoimmune diseases.

7. The method for chemotherapeutically treating immune diseases and disorders according to claim 6 in which the autoimmune disease is multiple sclerosis.

8. The method for chemotherapeutically treating immune diseases and disorders according to claim 1 in which the immune disease or disorder is contact allergic dermatitis.

9. The method for chemotherapeutically treating immune diseases and disorders according to claim 1 in which 10 to 500 mg. of the active ingredient is orally administered to an adult patient in regular intervals of one to three days.

10. The method for chemotherapeutically treating immune diseases and disorders according to claim 1 in which 20 to 590 mg. of the active ingredient is daily administered parenterally and preferably intramuscularly, to a adult patient in one to three injections.

11. The method for chemotherapeutically treating immune diseases and disorders according to clam 1 in which ointment containing 1 to 20% of the active ingredient is applied onto the affected area of the patient who is suffering from an allergic dermatitis.

12. The method for chemotherapeuticaly treating multiple sclerosis according to claim 9 in which said active ingredient is 3',5'-dichloro-2,4'-dihydroxybenzanilide.

* * * * *